(12) United States Patent
Grimm

(10) Patent No.: US 6,756,341 B2
(45) Date of Patent: Jun. 29, 2004

(54) NATURAL HERBICIDE FOR WEED REMOVAL

(76) Inventor: Scott A. Grimm, P.O. Box 656, Lakeland, FL (US) 33802

(*) Notice: Subject to any disclaimer, the term of this patent is extended or adjusted under 35 U.S.C. 154(b) by 0 days.

(21) Appl. No.: 10/304,807

(22) Filed: Nov. 26, 2002

(65) Prior Publication Data

US 2004/0102320 A1 May 27, 2004

(51) Int. Cl.[7] .................. A01N 25/00; A01N 63/00; A01N 59/00
(52) U.S. Cl. .................. 504/118; 504/119; 504/116; 514/783
(58) Field of Search .................. 504/118, 119, 504/116, 132; 514/783

(56) References Cited

PUBLICATIONS

Tworkoski, Thomas, Weed Science (2002), 50(4), 425–431.*

* cited by examiner

*Primary Examiner*—Sabiha Qazi
(74) *Attorney, Agent, or Firm*—Pendorf & Cutliff

(57) ABSTRACT

A natural herbicide for selectively removing weeds from desirable grass/turf, the active components of the natural herbcide being sodium bicarbonate, cinnamon, and wheat flour, with a color indicator included to identify the natural herbicide coverage area.

16 Claims, No Drawings

NATURAL HERBICIDE FOR WEED REMOVAL

BACKGROUND OF THE INVENTION

The present invention relates to a natural herbicide for weed removal, and more particularly, pertains to a natural herbicide made from non-toxic and environmentally safe components that selectively kills and controls crabgrass, chickweed, clover, and basket grass.

The use of herbicides to kill and control a broad spectrum of weeds is known in the prior art. More specifically, chemical herbicides heretofore devised and utilized are the main products used for the purpose of weed control for ornamental and agricultural plants. Control of weeds is very beneficial when it permits the selective control of such plants without concurrent injury to desirable vegetation.

Chemical herbicides are classified according to the type of activity they possess. A given compound may have more than one type of activity depending upon its mode of application and the rate at which it is applied. In addition, natural herbicides are usually classified as selective or non-selective pre-emergents or post-emergents. An effective pre-emergence herbicide is one, which is selective in its nature. This means that the compound can kill the seed and germinated seedlings of undesirable plants without harm to the seed and germinated seedlings of the desirable plant; there will not be any problem of over penetration of the soil by the herbicide. Post-emergence herbicides are applied after the plant and weed have reached a substantial height. In general, a compound found to have post-emergence activity would not be selective. Herbicide types include defoliants, desiccants, eradicants, systemics and selective herbicide, and related plant growth regulants.

One of the oldest and most successful selective herbicide is 2,4-dichlorophenoxy) acetic acid commonly known as 2,4-D, is a member of the phenoxy family of natural herbicides, which was the first widely used organic natural herbicide. The phenoxy herbicides were so effective and economical for selectively controlling broadleaf weeds in grass corps that they put selective weed control in the public spotlight worldwide. Since 1945, phenoxy herbicides have provided very economical, selective, postemergence control of broadleaf weeds in grass corps and noncropland. According to the National Agricultural Pesticide Impact Assessment Program, it was reported that the phenoxy herbicides have been used for approximately 51 years with little or no acute or chronic toxicity to humans. Yet, still there is indication that the National Cancer Institute and naturalists are not satisfied with studies that have findings showing no relationship between cancer and the use of phenoxy family of herbicides, specifically, 2-4 D.

Other commonly known chemical herbicides are as follows. Arsenical herbicides include cacodylic acid and the salts of monomethylarsinic acid and dimethylarsinic acid. Cacodylic acid is a defoliating or desiccating contact herbicide. Arsenic acid salts have lower contact toxicity and act through absorption.

Carbamate and thiocarbamate herbicides include Belanal, Betanex, Sutan, Eptam, and similar trademark products. These herbicides usually are applied to the soil and are taken up through the root systems.

Carboxylic acid herbicides are illustrated by commercial products such as Banvel, Garlon and 2,4-D. Various of these herbicides can be applied to the soil or to foliage, and are effective against broad leaf weeds.

Dinitroaniline herbicides include Balan and Treflan commercial products, which are applied to the soil to inhibit root growth and shoot growth, and exhibit low translocation.

Heterocyclic nitrogen-containing herbicides are illustrated by Aatrex, Basagran, Sencor and Velpar, which are applied to the soil for pre-emergent control.

Organophosphate compounds are useful as plant growth regulators and herbicides. This type of organic biocide structure is illustrated by Bensulide and Betasan.

Urea herbicides are nonselective and usually are soil applied. Urea-type commercial products include Lorox and Tupersan.

Quaternary herbicides include commercial products such as Avenge, Diquat and Paraquat, which have utility as contact foliars.

Finally, other commercially available herbicides include Atrazine, Bentazon, Bromacil, Casoron, Chloroamben, Delapon, Diuron, Fluometuron, Glphosate, Linuron, Picloram, Trifluralin, and the like.

Crabgrass/crows foot/goose grass is a coarse grass with a cluster of tillers that arise from a central part of the plant and has flattened stems. It belongs to the grass family poaceae and is reproduced primarily by seeds. Large crabgrass can be reproduced by long, rooting tillers. Most persons see crabgrass as a major weed that infests home lawns. Crabgrass has tremendous survival reproductive capabilities.

Crabgrass can be controlled by pre-emergence natural herbicides or post-emergence natural herbicides. Generally, the natural herbicide is chosen according to the type of turf grass desired. Popular pre-emergence herbicides used to control crabgrass are: benefin, DCPA, napropamide, bdnsulide, oryzaline, pendimethalin, dithiopyr, proiamine, atrazine, oxadiaxon, atrazine, and isoxaben. Commonly known post-emergence herbicides for control of crabgrass are: asulam, sethoxydim, MSMA and CMA.

Chickweed is low-growing, has bright green leaves and a small white flower with a star shape. Chickweed is part of the pink family Caryophyllaceae. Chickweed can be controlled by pre-emergence or post-emergence herbicides. Basket grass/Indian basket grass belongs to the lily family Liliaceae and is controlled by pre-emergence or post-emergence herbicides. Popular pre-emergence herbicides used to control chickweed, and basket grass are: benefin, DCPA, napropamide, bdnsulide, oryzaline, pendimethalin, dithiopyr, prolamine, atrazine, oxadiaxon, atrazine, and isocaben. Commonly known postemergence herbicides for control of chickweed and basket grass are: asulam, sethoxydim, MSMA and CMA.

Clover is another weed that is considered to be a nuisance. Clover is a perennial low-growing weed with a whitish flower. Clover spreads by seeds and generally has 3 dark green leaflets to a leaf. Clover belongs to the family Papilionaceae. The best way to control clover is with selective post-emergence herbicide.

U.S. Pat. No. 6,323,153 disclosed a method for controlling vegetation using herbicidal composition containing carboxylic or phoshonic acid salt. One of the vegatations being controlled is crabgrass. The carboxylic or phosphonic acid salt is an alkali salt of at least one acid selected from an aminopoycarboxylic acid, an aliphatic carboxylic acid, a hydroxycarboxylic acid, an amino acid, an ether polycarboxylic acid, a phosphonic acid and a polyposphonic acid.

There are at least four ways to control crabgrass without chemicals: 1) adjust the mowing height of your lawn mower so that the desired grass, tall grass, which requires a lot of nutrients to thrive; and as such, starves out the crabgrass; 2) fertilize more because the higher and healthier the desired grass grows, the more nutrients it steals from the crabgrass; 3) take black mulching paper of black plastic and cover the entire infested area for about ten days, this will kill the crabgrass; or 4) irrigate deeply and frequently, then do not water again until there is the first sign of drought stress. Researchers have found these chemical-free methods to be just as effective, though maybe not as quick, in eliminating these weeds.

Many of the four methods listed above can also be used to control chickweed, basket grass, and clover.

Therefore, it can be appreciated that there exists a continuing need for a non-toxic product that contains compounds that have been determined to be non-carcinogenic by the EPA, specifically, not having a rating in Class A, "known carcinogens," Class B, "probable carcinogens," or Class C, "Possible carcinogens." In this regard, the present invention fulfills this need.

BRIEF SUMMARY OF THE INVENTION

The present invention is a natural herbicide for weed removal that can be safely used by lawn care professionals or anyone desiring to control such weeds as crabgrass, chickweed, basket grass, and clover.

In light of the foregoing disadvantages revealed under the prior art, the present invention provides safe and easy use methods of selectively killing crabgrass, chickweed, basket grass, and clover, without harming the desired turf.

After the removal of Asulox® crabgrass killer from the market place, there remained no really effective and safe product for control of crabgrass in commercial and residential lawns. As such, the Applicant began experimenting with various inert products that are known to be safe; to determine which products or combination thereof would yield the desired results, killing crabgrass.

Accordingly, a primary function of the natural herbicide is selective crabgrass removal that is sate and quick, solving the problems inherent with the prior art references in use today. In testing the natural herbicide, Applicant discovered that the natural herbicide was effective at selective control of chickweed, basket grass, and clover. As such, the general purpose of the present invention will be described subsequently in detail.

To attain this, the present invention essentially consists of a natural herbicide, which has an effective amount of a composition comprising sodium bicarbonate, cinnamon, wheat flour, corn flour and Amarillo for color. The weeds may be killed by applying the composition when the weeds are on wet.

The composition of the invention acts as a selective natural herbicide. The composition may be mixed with a liquid carrying agent such as water to be sprayed onto the crabgrass. Since the mode of action appears to be through the blades of the crabgrass, there is little, if any, residual herbicidal effect in the ground. Further, all of the components of the composition are minimal risk inerts as termed by the Environmental Protection Agency. Therefore, it is to grow the desired turf adjacent, within, and around the treated area.

There has thus been outlined, rather broadly, the more important features of the invention in order that the detailed description thereof that follows may be better understood, and in order that the present contribution to the art may be better appreciated. There are, of course, additional features of the invention that will be described hereinafter, and which will form the subject matter of the claims appended hereto.

As such, those skilled in the art will appreciate that the conception, upon which this disclosure is based, may readily be utilized as a basis for the development of other compounds, methods, and systems for carrying out the several purposes of the present invention. It is important, therefore, that the claims be regarded as including such equivalent constructions insofar as they do not depart from the spirit and scope of the present invention.

It is therefore an object of the present invention to provide a powdered natural herbicide for selective weed removal.

It is therefore an object of the present invention to provide a powdered natural herbicide for selective crabgrass removal.

It is therefore an object of the present invention to provide a powdered natural herbicide for selective chickweed removal.

It is therefore an object of the present invention to provide a powdered natural herbicide for selective basket grass removal.

It is therefore an object of the present invention to provide a powdered natural herbicide for selective clover removal.

Another object of the present invention is to provide a liquid slurry of the natural herbicide composition which can be easily applied to the weed and have the same effectiveness as the powdered form of the natural herbicide.

An even further object of the present invention is to provide a natural herbicide for removal of such weeds as crabgrass, chickweed, basket grass and clover, which is susceptible of a low cost of manufacture with regard to both materials and labor, and which accordingly is then susceptible of low prices of sale to the consuming public, thereby making such natural herbicide economically available to the buying public.

These, together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be had to the descriptive matter in which there is illustrated the preferred embodiments of the invention.

DETAILED DESCRIPTION OF THE INVENTION

Unwanted weeds, such as crabgrass, chickweed, basket grass and clover, may be killed by covering the blades of the weeds with powdered or liquid slurry of a composition containing sodium bicarbonate cinnamon and wheat flour. To aid as an application indicator after application, a mixture of corn flour and Amarillo coloring is added to the composition.

More specifically, the present invention includes the active compounds of sodium bicarbonate and cinnamon. Through experimentation, Applicant found that 100% of sodium bicarbonate would kill grass, including crabgrass and other weeds. Further, sodium bicarbonate was light in weight or fine in composition, and alone was difficult to apply and would not adhere to the crabgrass. Furthermore, Sodium bicarbonate in its dry state was easily washed away or blown away without achieving effective results, killing the weeds.

Since the Applicant's intent was to kill crabgrass, the Applicant needed to decrease the strength of the sodium bicarbonate that is applied to the turf/grass. Additionally, the Applicant needed to find a way to get the sodium bicarbonate to adhere to the blades of the crabgrass. With continued experimentation, Applicant found that cinnamon and wheat flour, when added in combination with the sodium bicarbonate, formed a composition yielding the desired results, selective crabgrass killing. Cinnamon eliminated the harmful effects of the sodium bicarbonate on the desirable turf and aided in making the product more selective. Wheat flour allows the sodium bicarbonate and cinnamon to be easily dispersed and ensured that the powder compound adhered to the crabgrass blades. It is important to note that the addition of wheat flour and cinnamon allowed Applicant's composition to have the herbicidal effectiveness of a chemical natural herbicide without the toxic affects.

Applicant was desirous of having an indicator that would notify the natural herbicide user that the natural herbicide had been thoroughly and properly applied to the crabgrass. With even further experimentation, Applicant was able to increase the user friendliness of the product and discovered a means for indicating when the natural herbicide completely covered the crabgrass. Applicant experimented with various food colorings combined with the active compounds and applied the product to the crabgrass, without achieving the desired results. Continuing to test for the best indicators to show complete application of the natural herbicide, Applicant tested the food colorings in combination with other inert products such as bone meal, citrus meal, corn flour, corn meal, rye flour, soy flour, sugar, sand, grits, pepper, and rice flour. The test results showed that the combination of corn flour and. Amarillo, when added to the composition containing sodium bicarbonate, wheat flour, and cinnamon helped the user know when the crabgrass had. been completely covered. Specifically, in use, the composition is applied to wet/moist crabgrass; the area that is completely covered by the composition turns bright yellow, indicating complete coverage.

The experimentation resulted in the findings that the most effective active components of the composition are usually contained in an amount 20% to 80% by weight sodium bicarbonate, 1.85% to 0.95% by weight cinnamon, 78.15% to 19.05% by weight wheat flour, of the total composition. Preferably, when including the color indicator, the components of the composition is usually in an amount 20% to 80% by weight sodium bicarbonate, 1.85% to 0.95% by weight cinnamon, 77.63% to 17.5% by weight wheat flour, and 0.50% to 2.0% by weight corn flour and Amarillo coloring, of the total composition. In the preferred embodiment, the composition is 75.83% to 76% sodium bicarbonate, 22% to 22.75% wheat flour, and 0.95% cinnamon, with 0.47% to 1.05%, the balance of the composition, being corn flour and Amarillo.

In an effort to further ease application of the product, Applicant combined the above solid composition with a liquid carrier. Preferably, the liquid carrier is water. The composition, as set out above, is relatively insoluble in water; therefore, the composition with water is more a slurry. The slurry can be applied using various applicators. In the slurry form, the effective amount natural herbicide composition contained in the liquid carrier, is 20% to 98% by weight of the total composition of the slurry. Preferably, the effective of natural herbicide composition in the slurry form is 20% to 55% by weight of the slurry-with the liquid carrier being 80% to 45% by weight of the total composition of the slurry.

In experiments preformed with the powdered form and the liquid from of the herbicide were conducted at temperatures between 50 to 98 degrees Fahrenheit.

The following Examples will illustrate the practice of the present invention in its preferred embodiments. Other embodiments within the scope of the claims herein will be apparent to one skilled in the art from consideration of the specification and the practice of the invention as disclosed herein. It is intended that the specification, together with the examples, be considered exemplary only, with the scope and spirit of the invention being indicated by the claims, which follow.

EXAMPLE 1

A solid form of the composition containing 80% sodium bicarbonate by weight, 0.95% cinnamon by weight, 17.05% wheat flour by weight, and 0.50% corn flour and Amarillo by weight was applied to wet/moist crabgrass. The crabgrass was either wet/moist from the morning dew, or moisture was manually applied. The crabgrass was growing in a lawn of St. Augustine, Bahia or Bermuda turf. Upon immediate application, the crabgrass completely covered by the natural herbicide is bright yellow. The crabgrass begins to turn brownish in color in approximately 22 to 24 hours. The crabgrass was brown/black in color in 66 to 68 hours and completely dead. The daytime temperature at the time of spraying was about 70 degrees to 80 degrees Fahrenheit. The condition was clear and not overcast. None of the surrounding desirable grass was affected by the treatment, nor did any of the treated crabgrass grow back.

EXAMPLE 2

A similar experiment to Example 1 was preformed using solid form of the composition containing 75.83% sodium bicarbonate by weight, 0.95% cinnamon by weight, 22.75% wheat flour by weight and 0.47% corn flour and Amarillo by weight was applied to wet/moist crabgrass. The crabgrass, growing in a lawn of St. Augustine, Bahia or Bermuda turf, begins to turn brownish in color in approximately 24 to 28 hours. The crabgrass was brown/black in color in 68 to 72 hours and completely dead. The daytime temperature at the time of spraying was about 50 degrees to 60 degrees Fahrenheit. The condition was clear and not overcast. None of the surrounding desirable grass was affected by the treatment, nor did any of the treated crabgrass grow back.

EXAMPLE 3

A solid form of the composition containing 60% sodium bicarbonate by weight, 1.18% cinnamon by weight, 37.32% wheat flour by weight, and 1.5% corn flour and Amarillo by weight was applied to wet/moist crabgrass. The crabgrass, growing in a lawn of St. Augustine, Bahia or Bermuda turf, begins to turn brownish in color in approximately 24 to 28 hours. The crabgrass was brown/black in color in 68 to 72 hours and completely dead. The daytime temperature at the time of spraying was about 80 degrees to 85 degrees Fahrenheit. The condition was clear and not overcast. None of the surrounding desirable grass was affected by the treatment nor did any of the treated crabgrass grow back.

EXAMPLE 4

Using a solid form of the composition containing 40% sodium bicarbonate by weight, 1.66% cinnamon by weight, 56.59% wheat flour by weight, and 1.75% corn flour and Amarillo by weight was applied to wet/moist crabgrass. The crabgrass, growing in a lawn of St. Augustine, Bahia or Bermuda turf, begins to turn brownish in color in approximately 24 to 28 hours. The crabgrass was brown/black in color in 68 to 72 hours and completely dead. The daytime temperature at the time of spraying was about 85 degrees to 90 degrees Fahrenheit. The condition was clear and not overcast. None of the surrounding desirable grass was affected by the treatment nor did any of the treated crabgrass grow back.

EXAMPLE 5

Again using a solid form of the composition containing 20% sodium bicarbonate by weight, 1.85% cinnamon by weight, 76.15% wheat flour by weight, and 2.0% corn flour and Amarillo by weight was applied to wet/moist crabgrass. The crabgrass, growing in a lawn of St. Augustine, Bahia or Bermuda turf, begins to turn brownish in color in approximately 24 to 28 hours. The crabgrass was brown/black in color in 68 to 72 hours and completely dead. The daytime temperature at the time of spraying was about 85 to 90 degrees Fahrenheit. The condition was clear and not overcast. None of the surrounding desirable grass was affected by the treatment nor did any of the treated crabgrass grow back.

EXAMPLE 6

Taking the composition in Example 2 and making a slurry that contains 45% of a liquid carrying agent, preferably water and 55% composition. The slurry was then sprayed on crabgrass. The crabgrass, growing in a lawn of St. Augustine, Bahia or Bermuda turf, begins to turn brownish in color in approximately 24 to 28 hours. The crabgrass was brown/black in color in 68 to 72 hours and completely dead. The daytime temperature at the time of spraying was about 85 degrees to 90 degrees F. None of the turf in or around the treated area was affected.

EXAMPLE 7

Taking the composition in Example 2 and making a slurry that contains 80% of a liquid carrying agent, preferably water and 20% composition. The slurry was then sprayed on crabgrass. The crabgrass, growing in a lawn of St. Augustine, Bahia or Bermuda turf, begins to turn brownish in color in approximately 29 to 28 hours. The crabgrass was brown/black in color in 68 to 72 hours and completely dead. The daytime temperature at the time of spraying was about 85 degrees to 90 degrees Fahrenheit. None of the turf in or around the treated area was affected.

Applicant duplicated the Experiments set out above in Examples 1 through 7 with chickweed, basket grass and clover. The results were almost identical to the results discussed in the above experiments.

Although this invention has been described in its preferred form with a certain degree of particularity with respect to a natural herbicide for selective killing of crabgrass, it is understood that the present disclosure of the preferred form has been made only by way of example, and that numerous changes in the details of the composition of the combination may be resorted to without departing from the spirit and scope of the invention.

What I claim as my invention is:

1. A dry herbicidal composition for selective weed removal consisting essentially of:
   (a) sodium bicarbonate;
   (b) cinnamon; and
   (c) wheat flour.

2. The dry herbicidal composition as set forth in claim 1, further including a color indicator.

3. The dry herbicidal composition as set forth in claim 2 wherein the color indicator is comprised of corn flour and Amarillo.

4. The dry herbicidal composition as set forth in claim 2 wherein the weed is selected from the family of weeds consisting essentially of crabgrass, chickweed, basket grass and clover.

5. The dry herbicidal composition as set forth in claim 1, consisting essentially of:
   (a) 20 to 80% by weight sodium bicarbonate;
   (b) 1.85 to 0.95% by weight cinnamon; and
   (c) 78.15 to 19.05% by weight wheat flour.

6. A dry herbicidal composition for selective weed removal consisting essentially of:
   (a) 20 to 80% by weight sodium bicarbonate;
   (b) 1.85 to 0.95% by weight cinnamon;
   (c) 77.63 to 17.5% by weight wheat flour; and
   (d) 0.50 to 2.0% by weight color indicator.

7. The dry herbicidal composition as set forth in claim 6 wherein, the color indicator is corn flour and Amarillo.

8. The dry herbicidal composition as set forth in claim 6, wherein the weed is selected from the family of weeds consisting essentially of crabgrass, chickweed, basket grass and clover.

9. A slurry herbicidal composition for selective crabgrass removal consisting essentially of;
   (a) sodium bicarbonate;
   (b) cinnamon;
   (c) wheat flour; and
   (d) a carrying agent.

10. The slurry herbicidal composition as set forth in claim 9, wherein, the carrying agent is water.

11. The dry herbicidal composition as set forth in claim 9, wherein the weed is selected from the family of weeds consisting essentially of crabgrass, chickweed, basket grass and clover.

12. The slurry herbicidal composition as set forth in claim 10, wherein the effective amount of natural herbicide composition in the slurry is in an amount of 20% to 55% by weight of the slurry with the liquid carrier being 80% to 45% by weight of the slurry.

13. The method of removing weeds which comprises applying to the locus of the weed a herbicidally effective amount of a selective herbicidal composition consisting essentially of sodium bicarbonate, cinnamon and wheat flour.

14. The method of claim 13, wherein, the herbicidal composition, further including a color indicator.

15. The method of claim 14, wherein, the color indicator is corn flour and Amarillo.

16. The dry herbicidal composition as set forth in claim 13 wherein the weed is selected from the family of weeds consisting essentially of crabgrass, chickweed, basket grass and clover.

* * * * *